(12) United States Patent
Lin et al.

(10) Patent No.: US 12,040,069 B2
(45) Date of Patent: Jul. 16, 2024

(54) NEUROSTIMULATION THERAPY

(71) Applicant: International Business Machines Corporation, Armonk, NY (US)

(72) Inventors: Qinghuang Lin, Yorktown Heights, NY (US); Pritish Ranjan Parida, Cortlandt Manor, NY (US); Mohamed Ghalwash, Yorktown Heights, NY (US); Daby Mousse Sow, Croton on Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 130 days.

(21) Appl. No.: 17/218,744

(22) Filed: Mar. 31, 2021

(65) Prior Publication Data

US 2022/0319661 A1 Oct. 6, 2022

(51) Int. Cl.
| | |
|---|---|
| *G16H 20/30* | (2018.01) |
| *A61N 1/02* | (2006.01) |
| *A61N 1/36* | (2006.01) |
| *G16H 40/40* | (2018.01) |
| *G16H 50/50* | (2018.01) |
| *G16H 50/70* | (2018.01) |
| *A61N 1/05* | (2006.01) |

(52) U.S. Cl.
CPC ............ *G16H 20/30* (2018.01); *A61N 1/025* (2013.01); *A61N 1/36192* (2013.01); *G16H 40/40* (2018.01); *G16H 50/50* (2018.01); *G16H 50/70* (2018.01); *A61N 1/0551* (2013.01)

(58) Field of Classification Search
CPC ........ G16H 20/30; G16H 50/50; G16H 50/70; G16H 40/40; A61N 1/025; A61N 1/36192; A61N 1/0551
See application file for complete search history.

(56) References Cited

U.S. PATENT DOCUMENTS

| | | |
|---|---|---|
| 2017/0087302 A1 | 3/2017 | Osorio |
| 2018/0008827 A1 | 1/2018 | Dolev et al. |
| 2019/0022397 A1 | 1/2019 | Srivastava et al. |

OTHER PUBLICATIONS

Anonymous, "Method and System for Recognizing Pain Source in Users using Cognitive Techniques and Recommending Corrective Actions," IP.com No. IPCOM000255379D, IP.com Electronic Publication Date: Sep. 20, 2018, 4 pages.

*Primary Examiner* — Aryan E Weisenfeld
(74) *Attorney, Agent, or Firm* — Amin, Turocy & Watson, LLP

(57) ABSTRACT

Techniques regarding neuromodulation are provided. For example, one or more embodiments described herein can comprise a system, which can comprise a memory that can store computer executable components. The system can also comprise a processor, operably coupled to the memory, and that can execute the computer executable components stored in the memory. The computer executable components can include a mapping component that can generate a stimulus map by mapping a stimulus parameter to a response from an entity to application of a neuromodulating stimulus, with the first neuromodulating stimulus being applied to the entity based on the first stimulus parameter, to therapeutically cause or prevent a sensation.

20 Claims, 11 Drawing Sheets

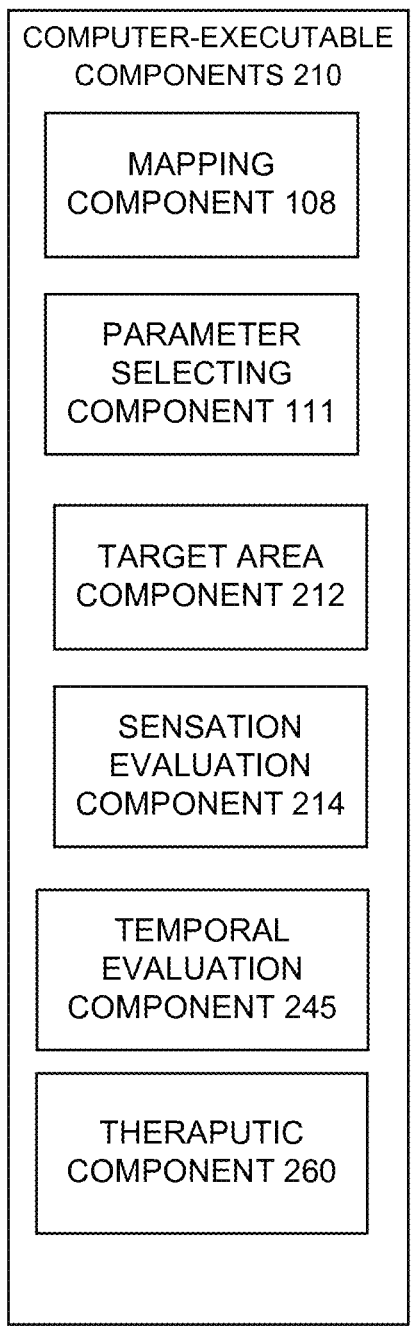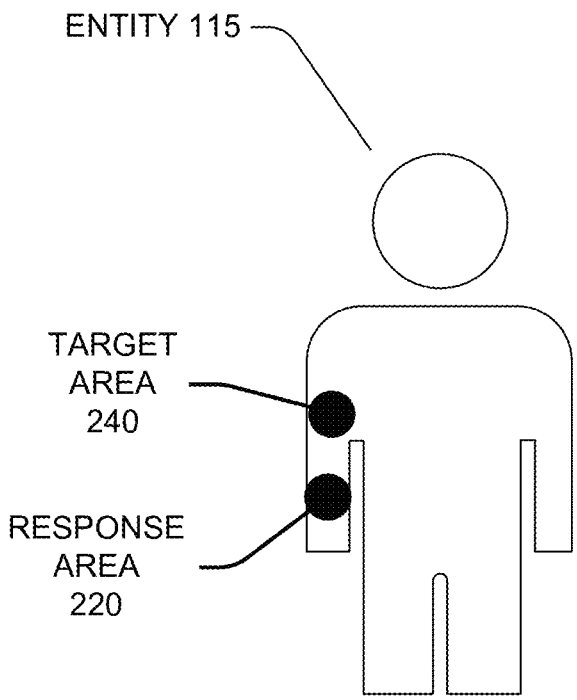
FIG. 2B
FIG. 2A

NEUROSTIMULATION THERAPY

BACKGROUND

One or more embodiments relate to electronic systems in healthcare, and more specifically, to adaptive systems based on mapping neurostimulation.

SUMMARY

The following presents a summary to provide a basic understanding of one or more embodiments of the disclosure. This summary is not intended to identify key or critical elements, or to delineate any scope of particular embodiments or any scope of the claims. Its sole purpose is to present concepts in a simplified form as a prelude to the more detailed description that is presented later. In one or more embodiments described herein, systems, computer-implemented methods, apparatuses and/or computer program products that can map results of neurostimulation applied to cause or prevent a sensation in an entity.

According to some embodiments described herein, a system is provided. The system can include a memory that stores computer executable components. The system can also include a processor, operably coupled to the memory, that can execute the computer executable components stored in the memory. The computer executable components can include a mapping component that can generate a stimulus map by mapping a first stimulus parameter to a response from an entity to application of a first neuromodulating stimulus, with the first neuromodulating stimulus being applied to the entity based on the first stimulus parameter. In the example system described, the response can include a result of an alteration of nerve activity of the entity by application of the first neuromodulating stimulus, and the stimulus map generated by the mapping component can be used by a treatment device that can alter nerve activity of the entity corresponding to the mapped areas.

In variations of the system embodiments, the system can further include a target area component that can select a target area of the entity, with the result including a response area of the entity where a result of the alteration of nerve activity was perceived by the entity. Further, the system can include a sensation evaluation component that can evaluate a similarity of the target area and the response area, with the mapping component further mapping the first stimulus parameter to the similarity, the response area, and the target area.

In some variations of the system embodiments, the first neuromodulating stimulus can be applied to a spinal region of the entity by an electrode of a spinal cord stimulation device, with the first stimulus parameter including, for some embodiments, an electrode fractionalization setting of the electrode that applied the signal. Further, the first stimulus parameter can include a characteristic of a stimulation pulse of the neuromodulating stimulus, and a stimulus area on the entity. In some variations of the system embodiments, the system can further include a parameter selecting component that can select the first stimulus parameter based on the target area.

In some variations, the first stimulus parameter can include a characteristic of a stimulation pulse of the neuromodulating stimulus, and a stimulus area on the entity, with the characteristic including one or more of a waveform amplitude of the signal, a pulse-rate of the signal, and a pulse-width of the signal. In additional variations the mapping component further can generate the stimulus map by mapping a second stimulus parameter to the response from the entity to application of the first neuromodulating stimulus and a second neuromodulating stimulus, with the second neuromodulating stimulus being applied to the entity based on the second stimulus parameter, and the characteristic of the stimulation pulse including an interference compensating characteristic of the signal. In addition, in implementations of the system, the response from the entity can be received based on a graphical depiction of the entity. Also, the stimulus map can be generated by the mapping component based on a dermatome.

According to one or more example embodiments, a computer-implemented method is provided. The computer-implemented method can include, based on a stimulus parameter, applying, by a device operatively coupled to a processor, a neuromodulating stimulus to an entity, and based on this stimulus, generating a stimulus map by mapping the stimulus parameter to the first result. In some implementations, the first result can be embodied in a paresthesia map of the entity, and generating the stimulus map comprises generating the stimulus map based on an analysis of the paresthesia map. Other features of some embodiments include, having the stimulus parameter selected based on a second result of a previous neuromodulating stimulus applied to the entity. Also, in some embodiments, based on the configuration parameter, the neuromodulating stimulus can be applied by device including but not limited to a spinal cord stimulation (SCS) device, a deep brain stimulation (DBS) device, a dorsal root ganglion (DRG) stimulation device, and a transcutaneous Electrical Neuromuscular Stimulation (TENS) device.

According to other example embodiments, a computer program product that maps a stimulus parameter (also termed a neurostimulation parameter for some examples herein) to a sensation perceived by an entity is provided. The computer program product can comprise a computer readable storage medium having program instructions embodied therewith. The program instructions can be executable by a processor to cause the processor to, based on a stimulus parameter, apply a neuromodulating stimulus to an entity, based on a result of this application, generating a stimulus map by mapping the stimulus parameter to the result.

Other embodiments may become apparent from the following detailed description when taken in conjunction with the drawings.

BRIEF DESCRIPTION OF THE DRAWINGS

FIG. 2A illustrates a block diagram of an example, non-limiting system that includes computer-executable components that can map results of neuro stimulation applied to cause or prevent a sensation in an entity, in accordance with one or more embodiments described herein.

FIG. 2B provides an example of neurostimulation applied to cause or prevent a sensation in a target area of an entity, in accordance with one or more embodiments described herein.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section. One or more embodiments are now described with reference to the drawings, with like referenced numerals being used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

It is noted that the claims and scope of the subject application, and any continuation, divisional or continuation-in-part applications claiming priority to the subject application, exclude embodiments (e.g., systems, apparatus, methodologies, computer program products and computer-readable storage media) directed to implanted electrical stimulation for pain treatment and/or management.

Figure 1:
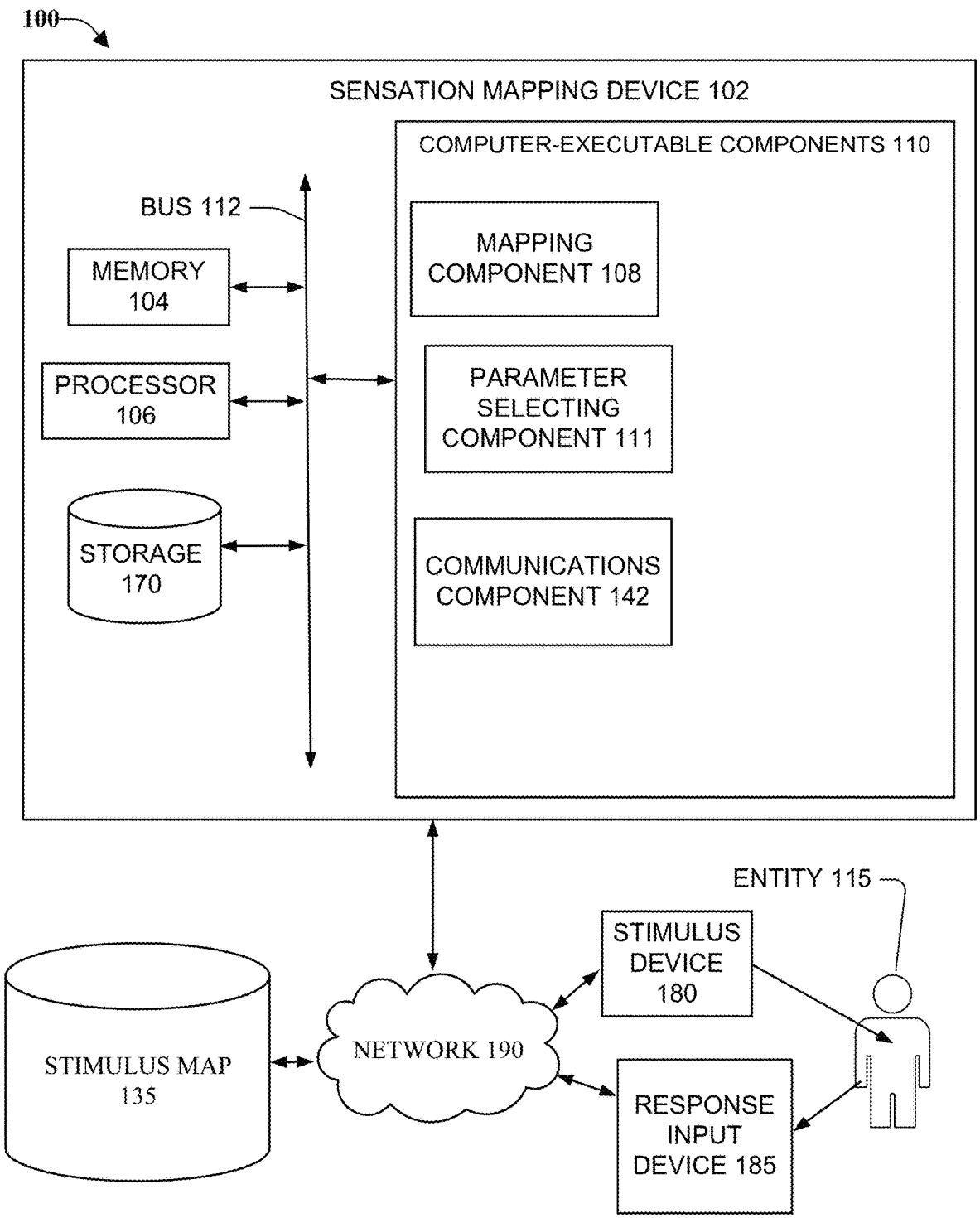
FIG. 1 illustrates a block diagram of an example, non-limiting system for the mapping of neurostimulation based on responses of an entity, in accordance with one or more embodiments described herein.

FIG. 1 illustrates a block diagram of an example, non-limiting system 100 for the mapping of neurostimulation to responses of an entity, in accordance with one or more embodiments described herein. Embodiments of systems (e.g., system 100 and the like), apparatuses or processes in various embodiments of the present disclosure can constitute one or more machine-executable components embodied within one or more machines, e.g., embodied in one or more computer readable mediums (or media) associated with one or more machines. Such components, when executed by the one or more machines, (e.g., computers, computing devices, virtual machines), can cause the machines to perform the operations described. Repetitive description of like elements and processes employed in respective embodiments is omitted for sake of brevity.

As shown in FIG. 1, some embodiments can comprise a system 100 that includes sensation mapping device 102 that can map neurostimulation to responses from an entity, in accordance with one or more embodiments described herein. In an example embodiment depicted, sensation mapping device 102 can be coupled, via network 190, to stimulus device 180, response input device 185, and stimulus map 135. In some embodiments, sensation mapping device 102 can comprise memory 104, processor 106, and computer-executable components 110, coupled to bus 112. It should be noted that, when an element is referred to herein as being "coupled" to another element, it can describe one or more different types of coupling. For example, when an element is referred to herein as being "coupled" to another element, it can be described one or more different types of coupling including, but not limited to, chemical coupling, communicative coupling, capacitive coupling, electrical coupling, electromagnetic coupling, inductive coupling, operative coupling, optical coupling, physical coupling, thermal coupling, and another type of coupling.

The system 100 can include any suitable computing device or set of computing devices that can be communicatively coupled to devices, non-limiting examples of which can include, but are not limited to, a server computer, a computer, a mobile computer, a mainframe computer, an automated testing system, a network storage device, a communication device, a web server device, a network switching device, a network routing device, a gateway device, a network hub device, a network bridge device, a control system, or any other suitable computing device. A device can be any device that can communicate information with the system 100 and/or any other suitable device that can employ information provided by system 100 and can enable computer-executable components 110, discussed below. As depicted, computer-executable components 110 can include mapping component 108, parameter selecting component 111, communications component 142, and any other components associated with sensation mapping device 102 and system 100 that can combine to provide different functions described herein.

Memory 104 can comprise volatile memory (e.g., random access memory (RAM), static RAM (SRAM), dynamic RAM (DRAM), etc.) and non-volatile memory (e.g., read only memory (ROM), programmable ROM (PROM), electrically programmable ROM (EPROM), electrically erasable programmable ROM (EEPROM), etc.) that can employ one or more memory architectures. Further examples of memory 104 are described below with reference to system memory 816 and FIG. 8. Such examples of memory 104 can be employed to implement any of the embodiments described herein.

In one or more embodiments, memory 104 can store one or more computer and machine readable, writable, and executable components and instructions that, when executed by processor 106 (e.g., a classical processor, and a quantum processor), can perform operations defined by the executable components and instructions. For example, memory 104 can store computer and machine readable, writable, and computer-executable components 110 and instructions that, when executed by processor 106, can execute the various functions described herein relating to sensation mapping device 102, including mapping component 108, parameter selecting component 111, communications component 142, and other components described herein with or without reference to the various figures of the one or more embodiments described herein.

Processor 106 can comprise one or more types of processors and electronic circuitry (e.g., a classical processor, and a quantum processor) that can implement one or more computer and machine readable, writable, and executable components and instructions that can be stored on memory 104. For example, processor 106 can perform various operations that can be specified by such computer and machine readable, writable, and executable components and instructions including, but not limited to, logic, control, input/output (I/O), arithmetic, and the like. In some embodiments, processor 106 can comprise one or more central processing unit, multi-core processor, microprocessor, dual microprocessors, microcontroller, System on a Chip (SOC), array processor, vector processor, quantum processor, and another type of processor. Further examples of processor 106 are described below with reference to processing unit 814 and FIG. 8. Such examples of processor 106 can be employed to implement any embodiments described herein.

According to multiple embodiments, storage 170 can include, but is not limited to, RAM, ROM, EEPROM, flash memory or other memory technology, solid state drive (SSD) or other solid-state storage technology, Compact Disk Read Only Memory (CD ROM), digital video disk (DVD), blu-ray disk, or other optical disk storage, magnetic cassettes, magnetic tape, magnetic disk storage or other magnetic storage devices, or any other medium which can be used to store information for embodiments and which can be accessed by the computer.

As depicted, memory 104, processor 106, mapping component 108, parameter selecting component 111, communications component 142, and any other component of sensation mapping device 102 described or suggested herein, can be communicatively, electrically, operatively, and optically coupled to one another via bus 112, to perform functions of system 100, sensation mapping device 102, and any components coupled thereto. Bus 112 can comprise one or more of a memory bus, memory controller, peripheral bus, external bus, local bus, a quantum bus, and another type of bus that can employ various bus architectures. Further examples of bus 112 are described below with reference to system bus 818 and FIG. 8. Such examples of bus 112 can be employed to implement any of the embodiments described herein.

System 100 can further include communications component 142, which can be used for transferring data and facilitating the exchange of information between the different system components of system 100 or between system 100 and one or more external elements. In some embodiments, communications component 142 can include internal storage, for example, memory. In some embodiments, the communications components 142 can serve to queue information between components and user device(s), such that the system operates in an efficient manner without excessive lag times. The communications component 142 can communicate information from a user interface, the information including, for example, response information from entity 115 regarding neurostimulation results. In one or more embodiments, communications component 142 can communicate with a cloud computing environment, such as the environment described with FIGS. 9 and 10 below.

In one or more embodiments described herein, sensation mapping device 102 can utilize mapping component 108 to perform (e.g., via processor 106) operations including, but not limited to, generation of stimulus map 135 by mapping a stimulus parameter to a response from entity 115 to application of a first neuromodulating stimulus to entity 115 based on the stimulus parameter. Stated differently, stimulus map 135 includes different combinations of settings for a stimulus to apply to entity 115 via stimulus device 180. In this example, a stimulus can be applied that provides an electrical current via electrodes of an SCS device positioned to provide the current to a particular location on the spine of entity 115, e.g., with the parameters including, but not limited to, the amount of current applied, and the position of the electrodes for an alteration of nerve activity of entity 115, e.g., causing or preventing impulses from sensory nerves that can cause or prevent a sensation perceived by the entity.

In one or more embodiments, stimulus device 180 can be a variety of different devices including a spinal cord stimulation (SCS) device, a deep brain stimulation (DBS) device, a dorsal root ganglion (DRG) stimulation device, and a transcutaneous Electrical Neuromuscular Stimulation (TENS) device. Different devices can apply a stimulus having a variety of different characteristics. In one or more embodiments, stimulus device 180 can receive instructions from mapping component 108 in the form of stimulus parameters generated by parameter selecting component 111. Different example characteristics of a stimulus that can be provided by stimulus device 180 are discussed below with FIG. 4.

In one or more embodiments, entity 115 can provide a response to the stimulus via response input device 185, e.g., a description of the results of the nerve activity caused the application of the stimulus. Continuing this example, in response to the stimulus having parameters selected by parameter selecting component 111, entity 115 can provide results that identify a particular part of entity 115 where a sensation was detected, along with other descriptive information about the sensation, such as intensity and type of sensation.

In one or more embodiments, mapping component 108 can receive the response from entity 115 to application of a the neuromodulating stimulus to entity 115 based on the stimulus parameters, e.g., the particular part of entity 115 where a sensation was detected, along with the other descriptive information about the sensation. Example sensations that can be mapped by mapping component 108 in one or more embodiments can broadly include different sensations at any point in the body. One type of sensation for which one or more embodiments can collect and use results information is sensations generated by the somatosensory system, e.g., felt in touch receptors of the skin. Example results that can be reported by an entity and mapped by embodiments include different types and intensity of sensation, including but not limited to cold, hot, smooth, rough, pressure, tickle, itch, vibrations, and more. Other types of sensation that can be reported by an entity include nausea, dizziness, and sensations of other parts of the body.

In some embodiments, the mapping process of mapping component 108 can include storing in stimulus map 135, a mapping of the selected parameters to the characteristics of the resulting sensation. One having skill in the relevant art(s), given the description herein, appreciates the stimulus map 135 can be incrementally generated over time, based on a selection of parameters by parameter selecting component 111, application of a stimulus based on the parameters via stimulus device 180, collection of response data via response input device 185, and mapping of the stimulus to the result via mapping component 108.

As discussed further with FIGS. 3-5 below, in accordance with one or more embodiments, mapping component 108 can store mappings between stimulus parameters and responses received in a data store that can be provided for different applications. Application of a stimulus to entity 115 in accordance with one or more embodiments is described with FIGS. 2-6 below, with FIGS. 2 and 6 discussing parameter generation, FIG. 3 discussing application of the stimulus, FIG. 4 discussing example stimulus parameters, and FIG. 5 discussing example approaches to receiving feedback from entity 115.

Stated differently, in some embodiments, based on combinations of stimulus parameters selected by parameter selecting component 111, feedback from the entity can be recorded, e.g., pairing combinations of parameters with results. In additional embodiments, this process can be repeated until a sufficiently accurate mapping between stimulus parameters and the response of entity 115 is achieved, e.g., a threshold of accuracy can be selected and established stimulus maps 135 can be tested by applying stimuli with different parameter combinations and identifying how closely the testing result matches the mapped response for the parameter combinations.

It should be appreciated that the embodiments described herein depict in various figures disclosed herein are for illustration only, and as such, the architecture of such embodiments are not limited to the systems, devices, and components depicted therein. For example, in some embodiments, system 100 and sensation mapping device 102 can further comprise various computer and computing-based elements described herein with reference to section below such as operating environment 900 of FIG. 9, cloud computing environment 1050 of FIG. 10, and the functional abstraction layers detailed with FIG. 11. In various embodiments, components of the system 100 (such as mapping component 108, parameter selecting component 111, and communications component 142) can include functional elements that can be implemented via cloud technologies, physical components (for example, computer hardware) and local software (for example, an application on a mobile phone or an electronic device).

FIG. 2A illustrates a block diagram of an example, non-limiting system 200 that includes computer-executable components that can map results of neuro stimulation applied to cause or prevent a sensation in an entity, in accordance with one or more embodiments described herein. As depicted, computer-executable components 210 can include mapping component 108, parameter selecting component 111, target area component 212, sensation evaluation component 214, therapeutic component 260, and other components described herein. Embodiments of systems (e.g., system 200 and the like), apparatuses or processes in various embodiments of the present disclosure can constitute one or more machine-executable components embodied within one or more machines, e.g., embodied in one or more computer readable mediums (or media) associated with one or more machines. Such components, when executed by the one or more machines (e.g., computers, computing devices, virtual machines), can cause the machines to perform the operations described. Repetitive description of like elements employed in one or more embodiments described herein is omitted for sake of brevity.

In additional embodiments, computer-executable components 210 can further include therapeutic component 260 that can use stimulus map 135 to therapeutically alter nerve activity of entity 115 to achieve a nerve activity result based on the stimulus map. For example, when used in a therapeutic setting, target area 240 can be selected as a location of entity 115 requiring therapy, e.g., a change in nerve activity in that location, such as removing a prickly sensation from the left arm of entity 115. In one or more embodiments, therapeutic component 260 can use information corresponding to target area 240 to retrieve parameter information from stimulus map 135, e.g., parameters mapped in stimulus map 135 to provide the therapeutic result for entity 115, that is, interfering with nerve activity such that the prickly sensation is not perceived by entity 115.

In this example, once the parameters are generated from stimulus map 135 by therapeutic component 260, stimulus device 180 can be used to apply a stimulus based on the parameters. Application of stimuli by example stimulus devices 180 is discussed further with FIG. 3 below, and development of stimulus map 135 to be used therapeutically for entity 115 and other entities is discussed further with FIGS. 4 and 7 below.

FIG. 2B provides an example of neurostimulation applied to cause or prevent a sensation in a target area of an entity, in accordance with one or more embodiments described herein. As depicted, entity 115 includes labels for target area 240 and response area 220. Repetitive description of like elements employed in one or more embodiments described herein is omitted for sake of brevity. As discussed further below, both target area 240 and response area 220 can correspond to parts of the body of entity 115. Because, in some implementations, the stimulus applied herein can cause sensations at any place in the body, the depicted areas do not only correspond to locations on the skin of entity 115. Rather, target area 240 and response area 220 can, in some embodiments, correspond to other parts of the body in addition to the skin. As described herein, causing a sensation for entity 115 can reference both results of a experiencing a sensation, where the sensation did not exist before, and also preventing a sensation that was existing when the stimulus was applied. In one or more embodiments, sensation evaluation component 214 can receive information about sensations caused by stimuli from a variety of sources, including but not limited to sensors for heart rate and temperature, as well as from a user interface that can capture body location sensory information from entity inputs.

In one or more embodiments, computer-executable components 210 can further include target area component 212 that can select target area 240 of entity 115. As described for some examples herein, target area 240 can be a selected part of entity 115 where a sensation having particular characteristics) is sought to be caused by a stimulus parameter selected by parameter selecting component 111. In some embodiments, computer-executable components 210 can further include sensation evaluation component 214 that can receive the described response from entity 115 via response input device 185, and compare this feedback with the intended target area 240, e.g., by assessing the similarity between target area 240 and response area 220.

In an example implementation, causing a sensation that did not exist before at a particular location or intensity, as well as prevention (or change in intensity) of an existing sensation can occur immediately after (e.g., within 30 seconds) or after a longer period of time, e.g., several days after the stimulation was first applied. In one or more embodiments, temporal evaluation component 245 can be used to measure the time period between application of the stimulus and the response by entity 115 that provides sensation details to sensation evaluation component 214, e.g., location, intensity, and type of sensation attributable to the stimulus.

In one or more embodiments, a result being in a steady state can refer to a condition when, for an entity 115, perception by the entity 115 of a sensation has no significant (e.g., measurable) change over time, e.g., received by sensation mapping device 102 and evaluated by sensation evaluation component 214. In one or more embodiments, the results of a stimulus can include both the sensation and location, and the period of time it took for the sensation at the location to reach a steady state. In addition to measuring a time period between application of a stimulus and a steady state of the resulting sensation, one or more embodiments can track the change in the sensations over the period of time before reaching the steady state. In one or more embodiments, temporal evaluation component 245 can further identify and track changes in sensations experienced over time, with this information being provided to sensation evaluation component 214 as additional characteristics of the sensation to be mapped by mapping component 108. For example, based on information provided by temporal evaluation component 245, multiple parameter sets for achieving a target result can be provided by parameter selecting component 111 to yield a target result having on onset over a range of time estimates. In another variation, multiple parameter sets for achieving the target result can be provided by embodiments along with a range of different time estimates for the duration the target result is estimated to last for entity 115, e.g., the durability of the target result for entity 115.

In another example of temporal aspects of sensations that can be measured and analyzed by temporal evaluation component 245 and sensation evaluation component 214, after a stimulus is applied, the sensation can affect a particular area (e.g., one inch diameter on the right arm of entity 115) with a particular sensation (e.g., a warm sensation), and over the time period after application of the stimulus before steady state is reached, any combination of the characteristics of the sensation can change, e.g., the location (e.g., right arm) can be the same, but the affected area size changes, and a different type of sensation can occur, e.g., the warm sensation detected by entity 115 can be reduced.

It is noted that, when sensation evaluation component 214 compares results collected by response input device 185 to target area 240, all of the characteristics of the sensation can be compared, including but not limited to, time to steady state, location, size, type of sensation, and change of sensation over time. In an example use of these components, the similarity measurement can be used to augment the mapping performed by mapping component 108. For example, in the mapping process, storing stimulus parameters with a location where a sensation was caused along with another location, sensation evaluation component 214, can provide additional information about both locations in the generated stimulus map. This component can also compare the temporal aspects of the target and the results, as described above.

In one or more embodiments, based on the comparison of the sensation at response area 220 to the response sought at target area 240, results can be stored in stimulus map 135. For example, in a situation where the parameters selected for a stimulus was mapped (e.g., by mapping component 108) in stimulus map 135 to cause or prevent a sensation at target area 240, but didn't cause the mapped sensation, an existing mapping for target area 240 can be revised by mapping component 108 to reflect this result. Similarly, when the mapped target area 240 in stimulus map 135 corresponds to response area 220, as predicted, this similarity can also be reflected in stimulus map 135.

Figure 3:
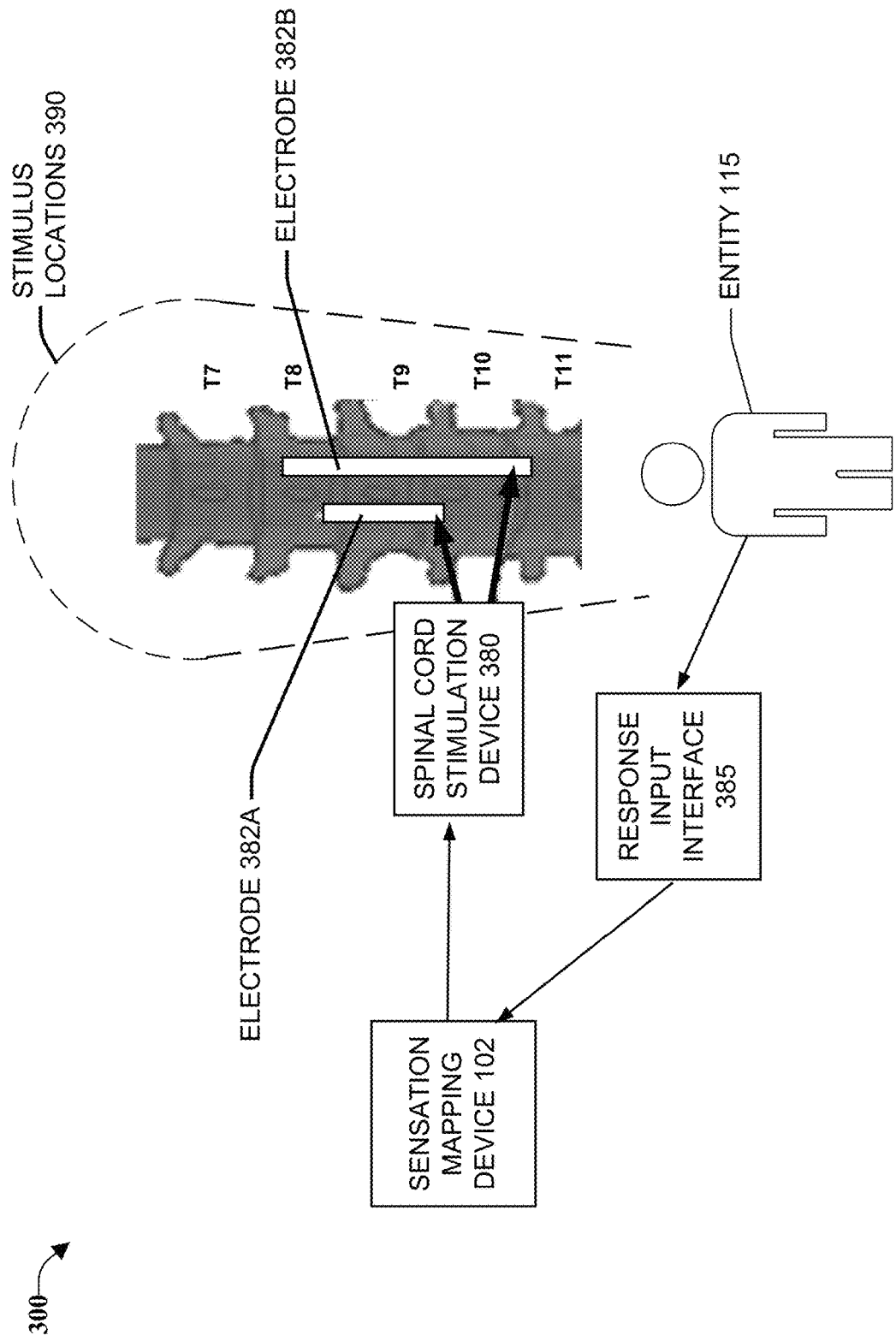
FIG. 3 illustrates a block diagram of an example, non-limiting system that can map neurostimulation parameters to entity responses, in accordance with one or more embodiments described herein.

FIG. 3 illustrates a block diagram of an example, non-limiting system 300 that can map neurostimulation parameters to entity responses, in accordance with one or more embodiments described herein. Repetitive description of like elements employed in one or more embodiments described herein is omitted for sake of brevity.

As depicted, system 300 includes sensation mapping device 102, spinal cord stimulation device 380, response input interface 385, and entity 115. To illustrate one approach to applying stimulation, FIG. 3 depicts an expanded view of stimulus locations 390, with these including locations on the body of entity 115 that can be entity to neurostimulation, e.g., the spinal cord, and brain. Spinal cord stimulation device 380 is depicted linked to electrodes 382A-B, placed to provide stimulation at particular ones of stimulus locations 390.

When one or more embodiments are employed to map stimulus parameters (e.g., the placement of electrodes 328A-B) to applying a stimulus to entity 115, mapping component 108 can be used to store a mapping between parameters applied by spinal cord stimulation device 380 and a response provided by entity 115 via response input interface 385.

Future implementations of neurostimulation for the same entity 115 can be beneficially affected by having mapping information corresponding to stimulus map 135 available. For example, with stimulus map 135, the increase in precision for placing electrodes 328A-B can in some circumstances result in fewer requirements to change the placement of electrodes and reducing the number of electrodes required to be placed to achieve a desired result. In other examples, having stimulus map 135 available for the placement of electrodes for entity 115, can also assist in the placement of electrodes for entities other than entity 115 (upon which the map is based). As described with FIG. 7 below, this benefit can result because, in some circumstances, the placement of electrodes for one entity can be useful for similar operations for other entities, e.g., portions of stimulus map 135 can be utilized as a universal stimulus map for other entities, in some circumstances.

FIG. 3 also depicts additional features of response input device 185. As depicted, response information from entity 115 can be collected by response input interface 385. It is noted that, one or more embodiments can utilize user interface designs that can flexibly capture many of the specific characteristics of the response of entity 115. FIG. 5 below details an example implementation where a graphical depiction of aspects of entity 115 can be used to capture response characteristics such as a location of a perceived sensation.

Figure 4:
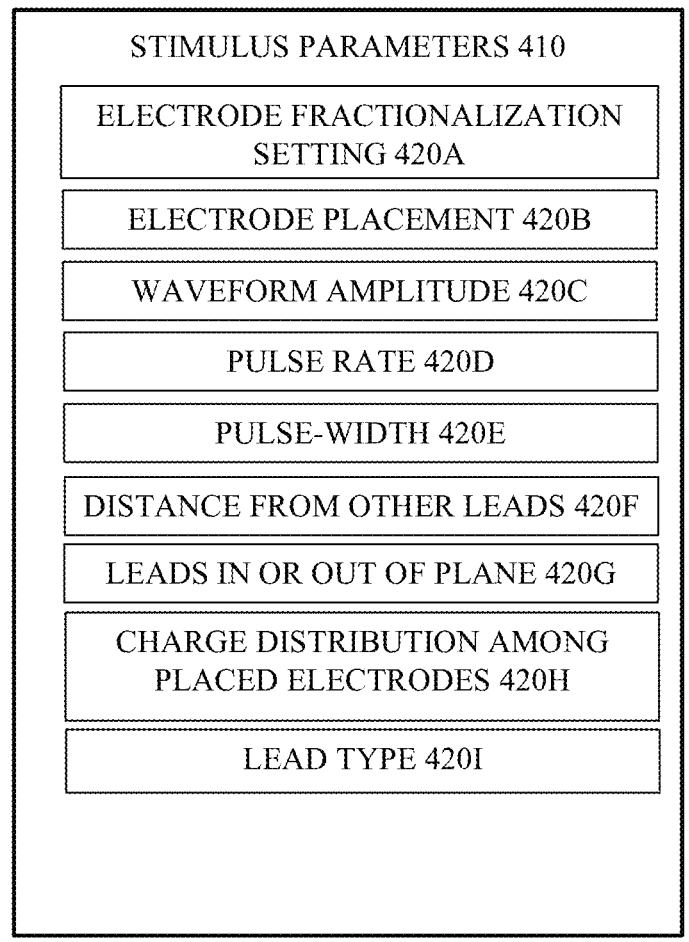
FIG. 4 illustrates a block diagram of an example, non-limiting system that can map neurostimulation parameters to entity responses, in accordance with one or more embodiments described herein.

FIG. 4 illustrates a block diagram of an example, non-limiting system 400 that can map neurostimulation parameters to entity responses, in accordance with one or more embodiments described herein. Repetitive description of like elements employed in one or more embodiments described herein is omitted for sake of brevity. As depicted, system 400 can include stimulus parameters 410. As used herein, stimulus parameters can control different aspects of how neurostimulation is applied to entity 115. As depicted, parameters 420A-420I provide a non-limiting set of example stimulus parameters that can be mapped to different results collected. Example parameters include, but are not limited to, electrode fractionalization setting 420A. In one or more embodiments, multiple electrodes placed at different locations can, in combination, provide the stimulus described herein, e.g., simultaneously or at different intervals. In this circumstance, a set amount of current can be provided to divide among the multiple electrodes and this parameter can be termed the electrode fractionalization setting 420A of the stimulus.

Additional characteristics can include electrode placement 420B, waveform amplitude 420C, pulse rate 420D, pulse-width 420E, distance from other leads 420F, leads in or out of plane 420G, charge distribution among placed electrodes 420H, lead type 420I, and other similar parameters useful for changing the application of neuromodulation signals by one or more embodiments.

As described with FIG. 2A above, in some implementations, a process with multiple stages can employed by mapping component 108 to initially test develop stimulus map 135, then in a deployment stage, therapeutic component 260 can utilize stimulus map 135 for the beneficial generation of sensations in entity 115 and other entities, e.g., with a universal stimulus map 135 described above.

For example, at the initial identification (also termed configuration, programming, or setup) stage, stimulus parameters can be selected by parameter selecting component 111 based on a combination of factors including, entity 115 medical information (e.g., age, medical history, heart rate), and SCS device 380 related information, e.g., data describing results of previously applied stimulus. At this stage, one or more embodiments of mapping component 108 can follow procedures for applying neurostimulation at a stage where results are largely unknown, e.g., embodiments of parameter selecting component 111 can select parameters that specify lower signal strengths based on a potential for higher strength signals applied by SCS device 380 to cause negative sensations for entity 115.

In this initial stage, the iterative approach described above with FIG. 3 can also be followed, with parameter selecting component 111 selecting parameters based on different characteristics of entity 115, e.g., accuracy of prior stimulus results, demographic information, and current condition. As described further with FIG. 7 below, when a level of accuracy is achieved (e.g., different levels based on efficacy requirements of therapeutic use of stimulus map 135) the generated stimulus map 135 can be deployed for use as a therapeutic resource for causing or preventing sensations for both entity 115 and potentially, other entities.

It is noted that, the generated stimulus map 135 can be used by therapeutic component 260 to guide a neuromodulating treatment device (e.g., SCS device 280) for therapeutically altering nerve activity of entity 115 in accordance with the stimulus parameters used to control neuromodulating treatment device. Thus, in an example implementation, a target result can be selected that includes a particular sensation (or suppression of a sensation) at target area 240 of an entity, and stimulus map 135 for the entity (or similar entities) can be interpreted by one or more embodiments of parameter selecting component 111 to provide parameters to SCS device 380 achieve the target result.

Figure 5:
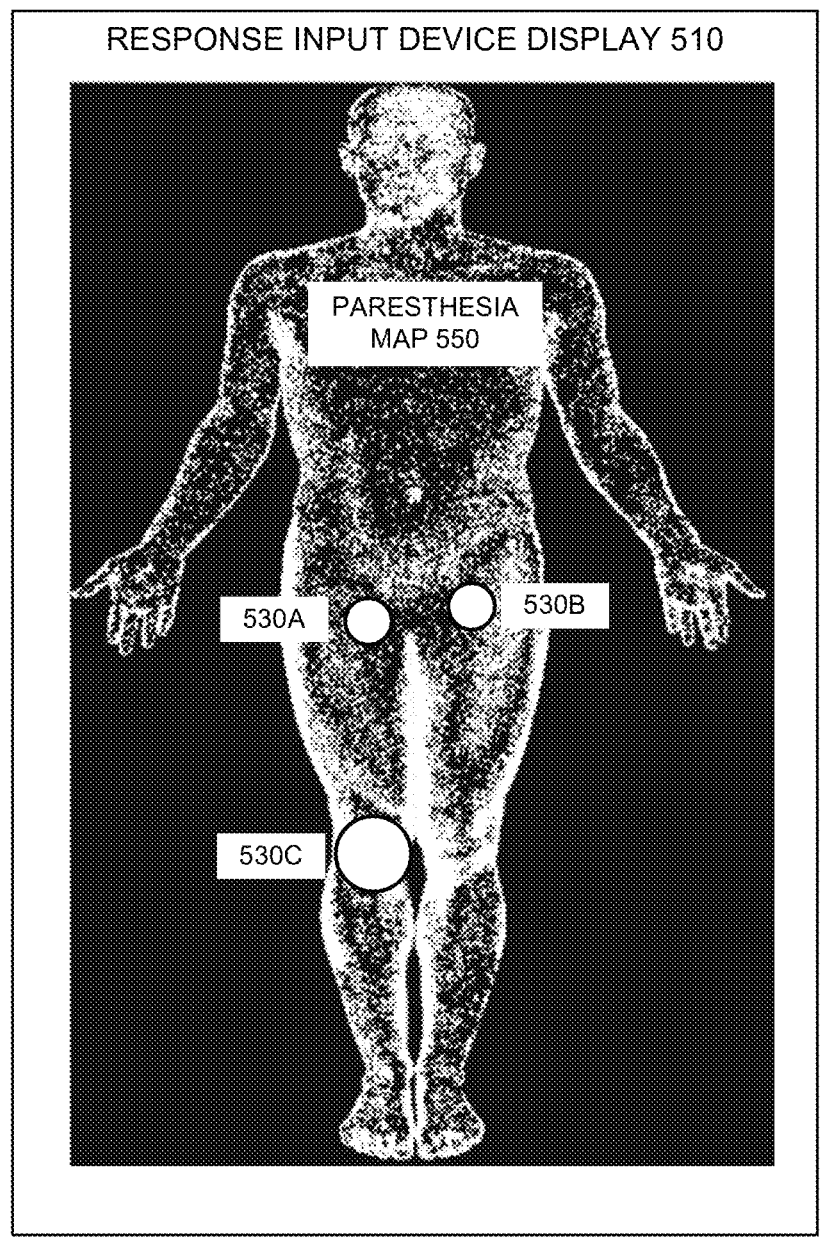
FIG. 5 illustrates a block diagram of an example, non-limiting system that can graphically capture sensations of an entity in response to a stimulus, in accordance with one or more embodiments described herein.

FIG. 5 illustrates a block diagram of an example, non-limiting system 500 that can graphically capture sensations of an entity in response to a stimulus, in accordance with one or more embodiments described herein. Repetitive description of like elements employed in one or more embodiments described herein is omitted for sake of brevity. In accordance with one or more embodiments, system 500 can include response input device display 510 as an input component of response input device 185. In an example implementation of response input device 185, response input device display 510 displays a graphic termed paresthesia map 550 with sensations 530A-C.

As discussed above, one aspect of one or more embodiments is to collect potentially detailed results of the application of one or more neuromodulation stimuli, with these results being incorporated into a map of stimulus applications sites to results. One approach that one or more embodiments can use to promote the accuracy and detail in stimulus map 135 utilizes a display user interface that accepts input overlayed over a diagram of potential sensation sites, e.g., sensations 530A-C highlighted by entity 115 in the human diagram of FIG. 5. In an example implementation of a response diagram, response input device 185 can display paresthesia map 550 (also termed paresthesia diagram). One having skill in the relevant art(s), given the description of embodiments herein, will appreciate that by enabling entity 115 to alter paresthesia map 550, not only can the location of sensations be mapped, the intensity and type of sensation can also be provided in the response.

In other implementations, system 500 can receive responses from entity 115 using additional approaches that include the use of natural language processing to extract the one or more features, wherein the one or more features can be n-grams (e.g., unigrams and/or bigrams), modal verbs, action verbs, and the like from one or more sentences describing sensations experienced by entity 115.

Figure 6:
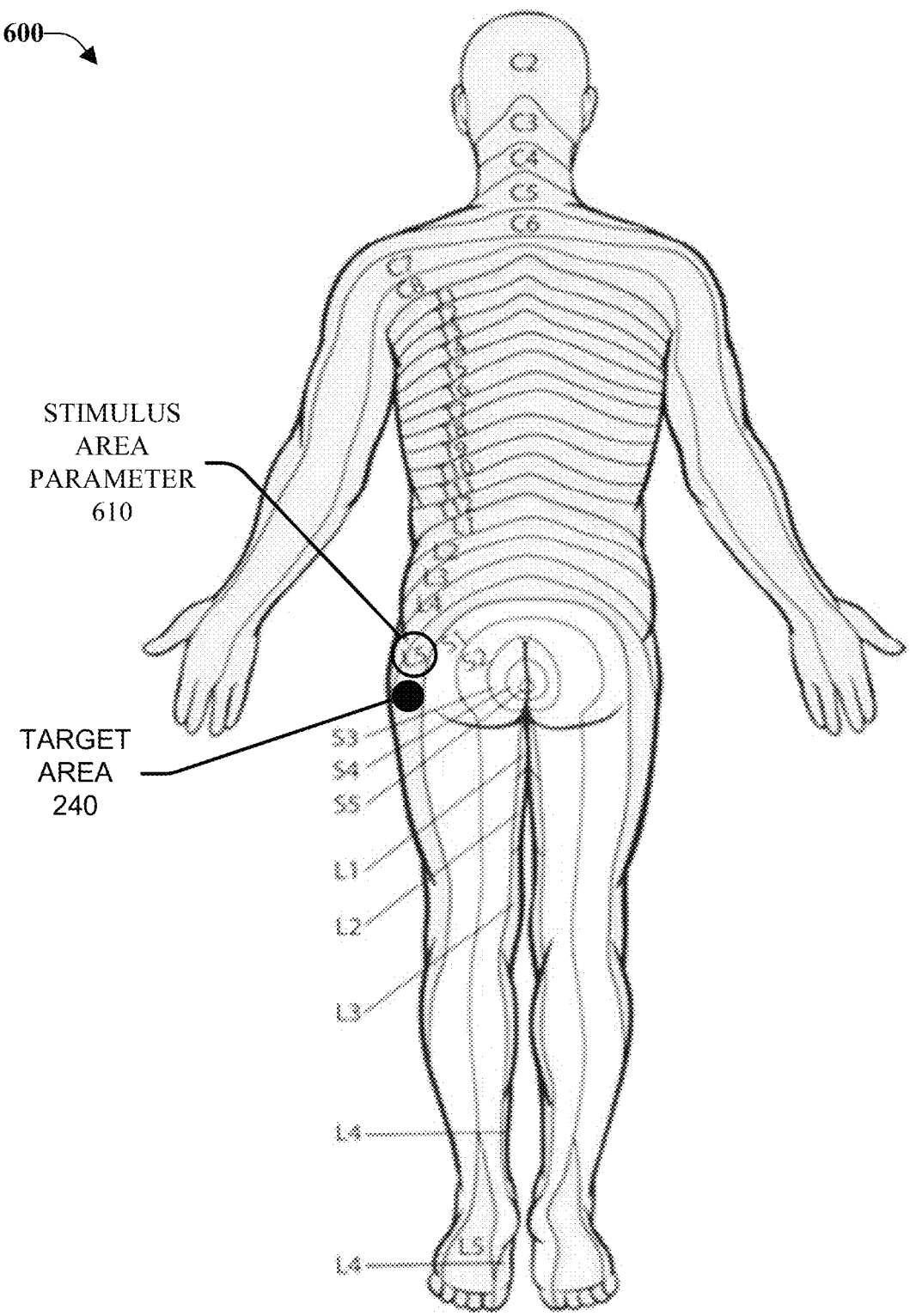
FIG. 6 illustrates a block diagram of an example, non-limiting system that can map neurostimulation parameters to entity responses, in accordance with one or more embodiments described herein.

FIG. 6 illustrates a block diagram of an example dermatome 600 that can provide an example source of stimulus parameters for application of a neuromodulating stimulus to entity 115, in accordance with one or more embodiments described herein. Repetitive description of like elements employed in one or more embodiments described herein is omitted for sake of brevity.

As noted above, one or more embodiments can select different stimulus parameters to control the application of a neuromodulating stimulus. As noted with FIG. 2 above, in some implementations, a target area 240 can be selected as a desired location for sensations to be perceived by entity 115. One way stimulus parameters can be selected so as to affect target area 240 is to provide dermatome 600 as a reference. For example, in a circumstance where target area 240 corresponds to the labeled (L5) band of dermatome 600, this vertebra can be selected as an electrode placement 420B as stimulus parameter 610 for use as a starting point for testing, or other uses. It is noted, based on the descriptions herein, that one or more embodiments, by mapping sensations to stimulus locations, can generate additional dermatome data, with additional stimulus parameter information (e.g., signal characteristics, electrode type, and multi-electrode information) to provide a more extensive dermatome.

Figure 7:
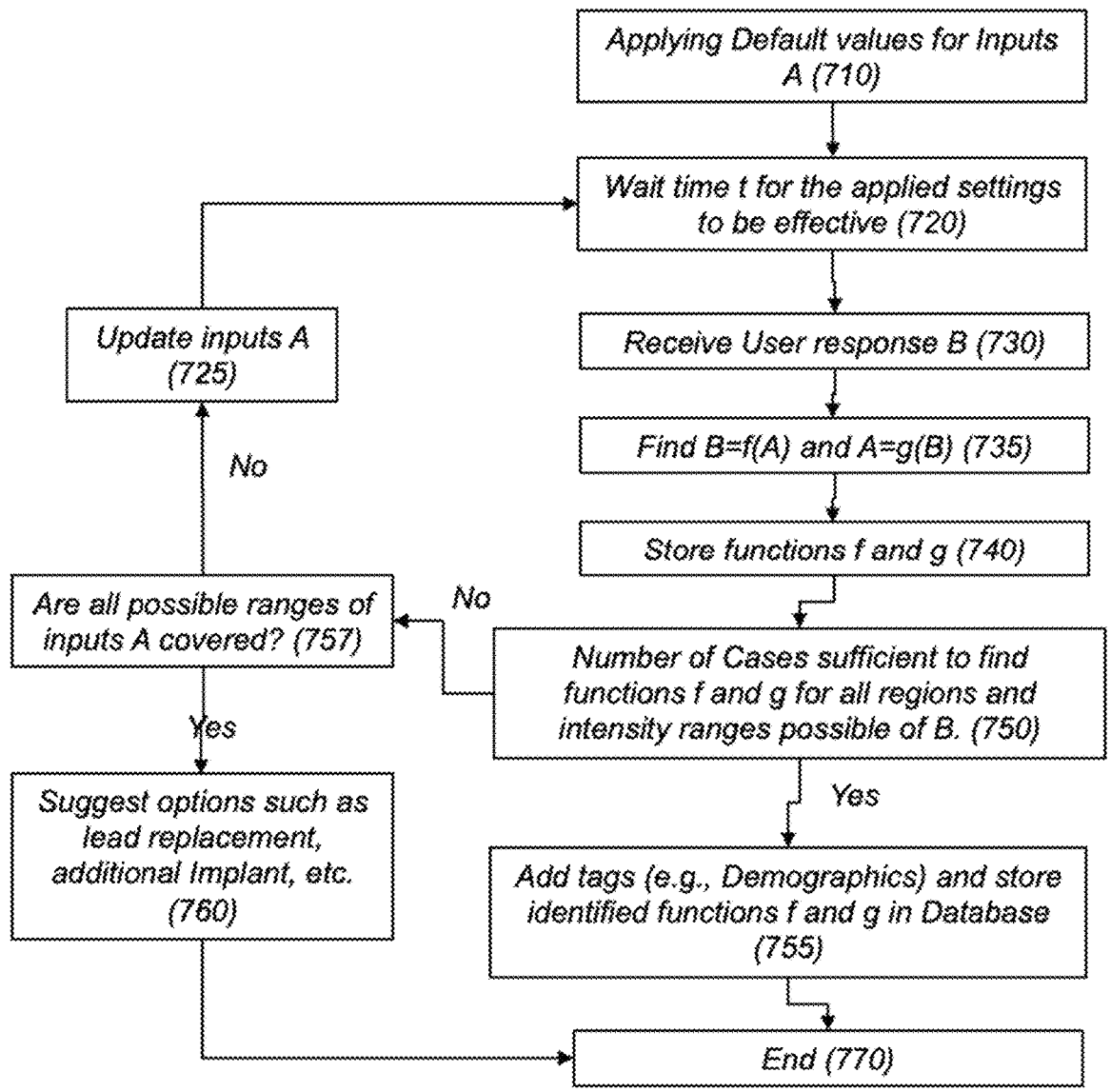
FIG. 7 illustrates a flow diagram of an example, non-limiting computer-implemented process that can map neurostimulation parameters to entity responses (e.g., identifying dermatome mapping), in accordance with one or more embodiments described herein.

FIG. 7 illustrates a flow diagram of an example, non-limiting computer-implemented process 700 that can map neurostimulation parameters to entity responses (e.g., identifying the dermatome mapping of example dermatome 600), in accordance with one or more embodiments described herein. Repetitive description of like elements and processes employed in respective embodiments is omitted for sake of brevity.

In another example application of mapping component 108, parameter selecting component 111, and sensation evaluation component 214, an iterative process can be performed where parameter selecting component 111 can select test parameters for iterations of stimulation, and, based on the similarity between the sensations of resulting response area 220 and target area 204 assessed by sensation evaluation component 214, stimulus map 135 can be increased in scope to cover more nerve stimulation aspects of entity 115. In an example described below, stimulus parameters selected by parameter selecting component 111 are represented as stimulus inputs (A), response sensations experienced by entity 115 are represented as entity response (B).

In the example of the iterative approach depicted in FIG. 7, at 710 an initial, default value can be applied for the stimulus inputs (A), e.g., selected by parameter selecting component 111 based on general initial values or initial values derived from previous stimuli applied to entity 115. At 720, during a period of time (t), entity 115 can be evaluated by sensation evaluation component 214 to determine whether the applied settings are effective to achieving a goal result, e.g., whether response area 220 matches target area 240 to a threshold level of similarity, e.g., 80%. At 730, an entity response (B) can be received via response input device 185 and evaluated by sensation evaluation component 214.

Continuing the description of this example, in one or more embodiments, at 735 mapping component 108 can generate a function (f) corresponding to stimulus map 135, such that applying stimulus input (A) as a parameter to function (f) is expected to result in entity response (B), e.g., f(A)=B or f (parameter applied)=particular sensation in right arm. Similarly, mapping component 108 can further generate a function (g) that can be the inverse function of function (f), that is such that entity response (B) as a parameter to function (g) results in the parameters that can be utilized as stimulus input (A) to achieve entity response (B), e.g., g(B)=A or g (particular sensation in right arm)=parameter applied.

At 740, once generated by mapping component 108, functions (f) and (g) can be stored for further accuracy testing, e.g., with additional parameters selected by parameter selecting component 111 and applied by mapping component 108 via stimulus device 180, with results collected by response input device 185 and analyzed by sensation evaluation component 214. At 750, once a sufficient number of cases have been observed to find functions (f) and (g) descriptive for a selected number of regions and intensity ranges of entity response (B) that are possible, stimulus map 135 can be used beyond the iterative, testing phase, and can be used for regular, therapeutic uses. In some embodiments, the number of cases can be determined to be sufficient if criteria are met including, but not limited to, a level of accuracy, and a level of coverage of different sensory areas of entity 115. When the number of cases is not determined to be sufficient, at 757 at 757, checks can be applied by mapping component 108 to the function testing, such as an inquiry as to whether selected possible ranges of input for stimulus input (A) have been applied, with further parameter testing by mapping component 108 at 725, with updated parameters selected by parameter selecting component 111 for stimulus input (A), e.g., to increase the number of ranges tested. Alternatively, when a range of selected possible ranges is determined by mapping component 108 to be covered, at 760, one or more embodiments can provide troubleshooting suggestions including, but not limited to replacing leads and adding additional implants to stimulus device 180.

As would be appreciated by one having skill in the relevant art(s), given the description herein, in additional embodiments, at the therapeutic stage (e.g., once a sufficient number of cases have been observed to find functions (f) and (g) descriptive for a selected number of regions and intensity ranges of entity response (B) that are possible) stimulus map 135 can further be used for treatment of other entities, e.g., based on demographic similarities with entity 115 and other similarity criteria. Thus, process 700 can end at 755 with a database (e.g., stimulus map 135) being updated by mapping component 108 with demographic metadata of entity 115, e.g., based on an approach where entities having similar demographic characteristics likely will have similar results when receiving stimuli having similar parameters.

In one or more embodiments, sensation mapping device 102 can employ hardware and/or software to solve problems that are highly technical in nature, including improving the therapeutic application of neurostimulation signals. One having skill in the relevant art(s), given the disclosure herein, would appreciate that the technical problems that can be solved by one or more embodiments described herein are not abstract and cannot be performed as a set of mental acts by a human. For example, the iterative processes described above performed by components including, parameter selecting component 111, mapping component 108, sensation evaluation component 214, and other components of methods and systems described herein, at least because of the complex characteristics of stimulus applied (e.g., described with FIG. 4 above) and the detailed mapping required by mapping component 108, are not abstract and cannot be performed as a set of mental acts by a human.

Further, in certain embodiments, some of the processes performed can be performed by one or more specialized computers (e.g., one or more specialized processing units, a specialized computer such as tomography and reconstruction, statistical estimation, and so on) for carrying out defined tasks related to precisely applying neurostimulation signals. As described herein, sensation mapping device 102 improve processes associated with the application of neurostimulation signals in the limited areas described and suggested by one or more embodiments herein. One or more embodiments, in addition to improving approaches to solving existing problems applying neurostimulation, also can be employed to solve new problems that arise through advancements in technologies mentioned above, computer architecture, and/or the like.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more components of computer program instructions, encoded on computer storage medium for execution by, or to control the operation of, information/data processing apparatus. Alternatively, or in addition, the program instructions can be encoded on an artificially generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices). The operations described herein can be implemented as operations performed by an information/data processing apparatus on information/data stored on one or more computer-readable storage devices or received from other sources.

Figure 8:
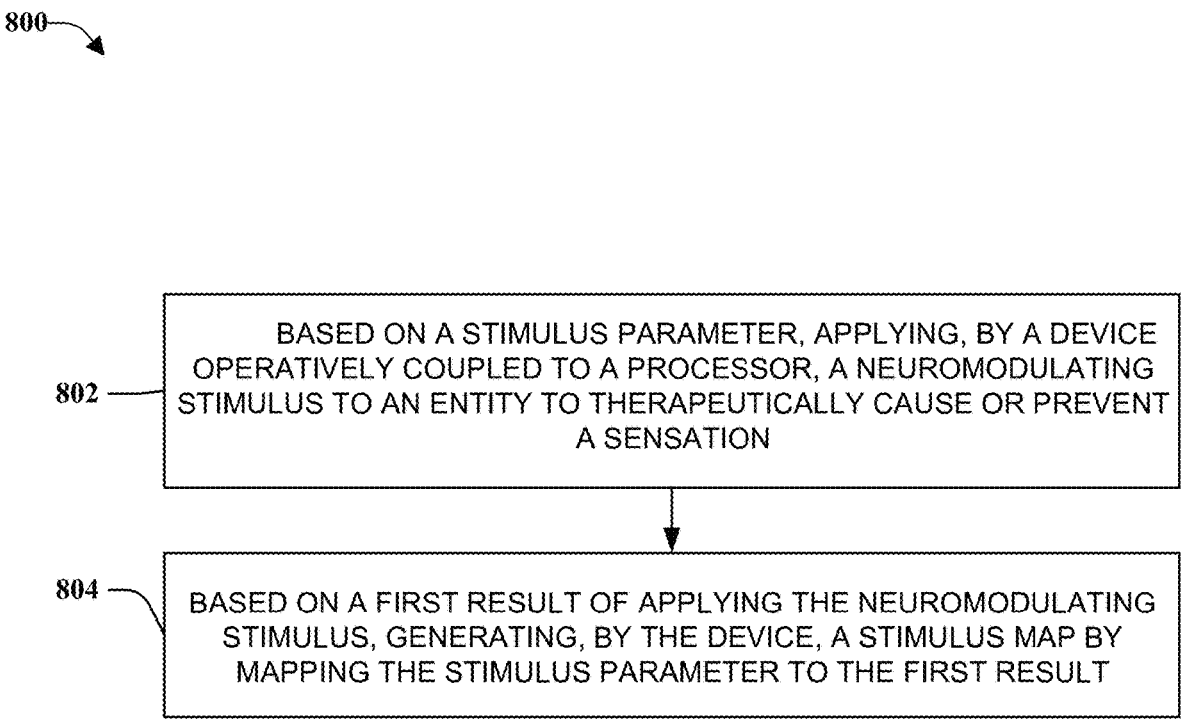
FIG. 8 illustrates a flow diagram of an example, non-limiting computer-implemented method that can map neurostimulation parameters to entity responses, in accordance with one or more embodiments described herein.

FIG. 8 illustrates a flow diagram of an example, non-limiting computer-implemented method 800 that can map neurostimulation parameters to entity responses (e.g., via sensation mapping device 102), in accordance with one or more embodiments described herein. Repetitive description of like elements and processes employed in respective embodiments is omitted for sake of brevity.

At 802, computer-implemented method 800 can include, based on a stimulus parameter, applying, by a device operatively coupled to a processor, a neuromodulating stimulus to an entity (via mapping component 108 facilitating application by stimulus device 180). For example, in one or more embodiments, computer-implemented method 800 can include, based on a stimulus parameter, applying (e.g., by spinal cord stimulation device 380), a neuromodulating stimulus selected by parameter selecting component 111 to entity 115.

At 804, computer-implemented method 800 can include, based on a first result of applying the neuromodulating stimulus, generating, by the device, a stimulus map by mapping the stimulus parameter to the first result (via sensation evaluation component 214 providing mapping information to mapping component 108. For example, in one or more embodiments, computer-implemented method 800 can include, based on a first result of applying the neuromodulating stimulus (e.g., revied by response input device 185), generating, by mapping component 108 of sensation mapping device 102, stimulus map 135 by mapping the stimulus parameter selected by parameter selecting component 111 to the first result, e.g., as discussed with FIG. 7 above.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more components of computer program instructions, encoded on computer storage medium for execution by, or to control the operation of, information/data processing apparatus. Alternatively, or in addition, the program instructions can be encoded on an artificially generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

Figure 9:
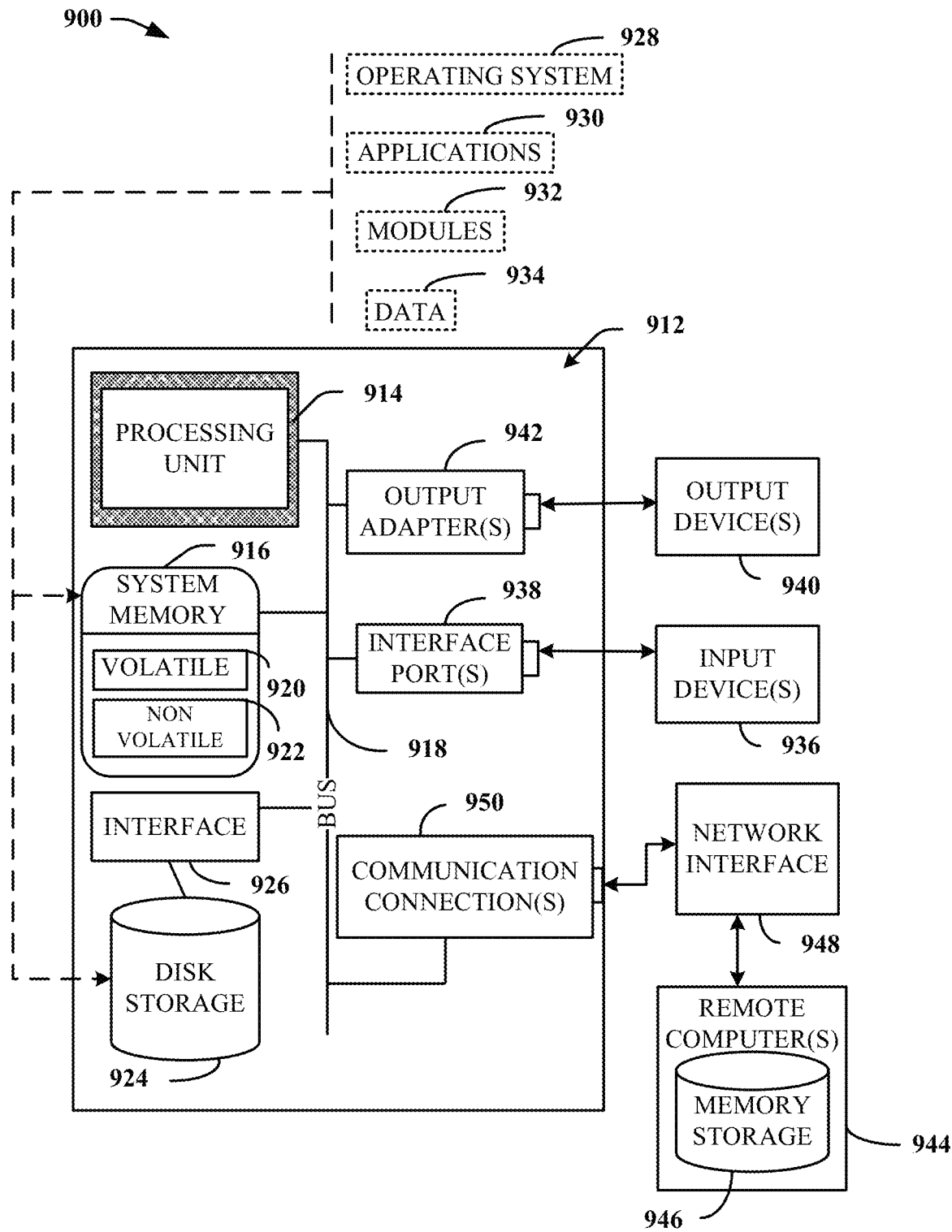
FIG. 9 illustrates a block diagram of an example, non-limiting operating environment in which one or more embodiments described herein can be facilitated.

In order to provide a context for the various aspects of the disclosed subject matter, FIG. 9 as well as the following discussion are intended to provide a general description of a suitable environment in which the various aspects of the disclosed subject matter can be implemented. FIG. 9 illustrates a block diagram of an example, non-limiting operating environment in which one or more embodiments described herein can be facilitated. Repetitive description of like elements employed in other embodiments described herein is omitted for sake of brevity.

With reference to FIG. 9, a suitable operating environment 900 for implementing various aspects of this disclosure can also include a computer 912. The computer 912 can also include a processing unit 914, a system memory 916, and a system bus 918. The system bus 918 couples system components including, but not limited to, the system memory 916 to the processing unit 914. The processing unit 914 can be any of various available processors. Dual microprocessors and other multiprocessor architectures also can be employed as the processing unit 914. The system bus 918 can be any of several types of bus structure(s) including the memory bus or memory controller, a peripheral bus or external bus, and a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 916 can also include volatile memory 920 and nonvolatile memory 922. The basic input/output system (BIOS), containing the basic routines to transfer information between elements within the computer 912, such as during start-up, is stored in nonvolatile memory 922. Computer 912 can also include removable/non-removable, volatile/non-volatile computer storage media. FIG. 9 illustrates, for example, a disk storage 924. Disk storage 924 can also include, but is not limited to, devices like a magnetic disk drive, floppy disk drive, tape drive, Jaz drive, Zip drive, LS-90 drive, flash memory card, or memory stick. The disk storage 924 also can include storage media separately or in combination with other storage media. To facilitate connection of the disk storage 924 to the system bus 918, a removable or non-removable interface is typically used, such as interface 926. FIG. 9 also depicts software that acts as an intermediary between users and the basic computer resources described in the suitable operating environment 900. Such software can also include, for example, an operating system 928. Operating system 928, which can be stored on disk storage 924, acts to control and allocate resources of the computer 912.

System applications 930 take advantage of the management of resources by operating system 928 through program modules 932 and program data 934, e.g., stored either in system memory 916 or on disk storage 924. It is to be appreciated that this disclosure can be implemented with various operating systems or combinations of operating systems. A user enters commands or information into the computer 912 through input device(s) 936. Input devices 936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 914 through the system bus 918 via interface port(s) 938. Interface port(s) 938 include, for example, a serial port, a parallel port, a game port, and a universal serial bus (USB). Output device(s) 940 use some of the same type of ports as input device(s) 936. Thus, for example, a USB port can be used to provide input to computer 912, and to output information from computer 912 to an output device 940. Output adapter 942 is provided to illustrate that there are some output devices 940 like monitors, speakers, and printers, among other output devices 940, which require special adapters. The output adapters 942 include, by way of illustration and not limitation, video and sound cards that provide a means of connection between the output device 940 and the system bus 918. It should be noted that other devices and systems of devices provide both input and output capabilities such as remote computer(s) 944.

Computer 912 can operate in a networked environment using logical connections to one or more remote computers, such as remote computer(s) 944. The remote computer(s) 944 can be a computer, a server, a router, a network PC, a workstation, a microprocessor-based appliance, a peer device or other common network node and the like, and typically can also include many or all of the elements described relative to computer 912. For purposes of brevity, only a memory storage device 946 is illustrated with remote computer(s) 944. Remote computer(s) 944 is logically connected to computer 912 through a network interface 948 and then physically connected via communication connection 950. Network interface 948 encompasses wire and wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 950 refers to the hardware/software employed to connect the network interface 948 to the system bus 918. While communication connection 950 is shown for illustrative clarity inside computer 912, it can also be external to computer 912. The hardware/software for connection to the network interface 948 can also include, for exemplary purposes only, internal and external technologies such as, modems including regular telephone grade modems, cable modems and DSL modems, ISDN adapters, and Ethernet cards.

Figure 10:
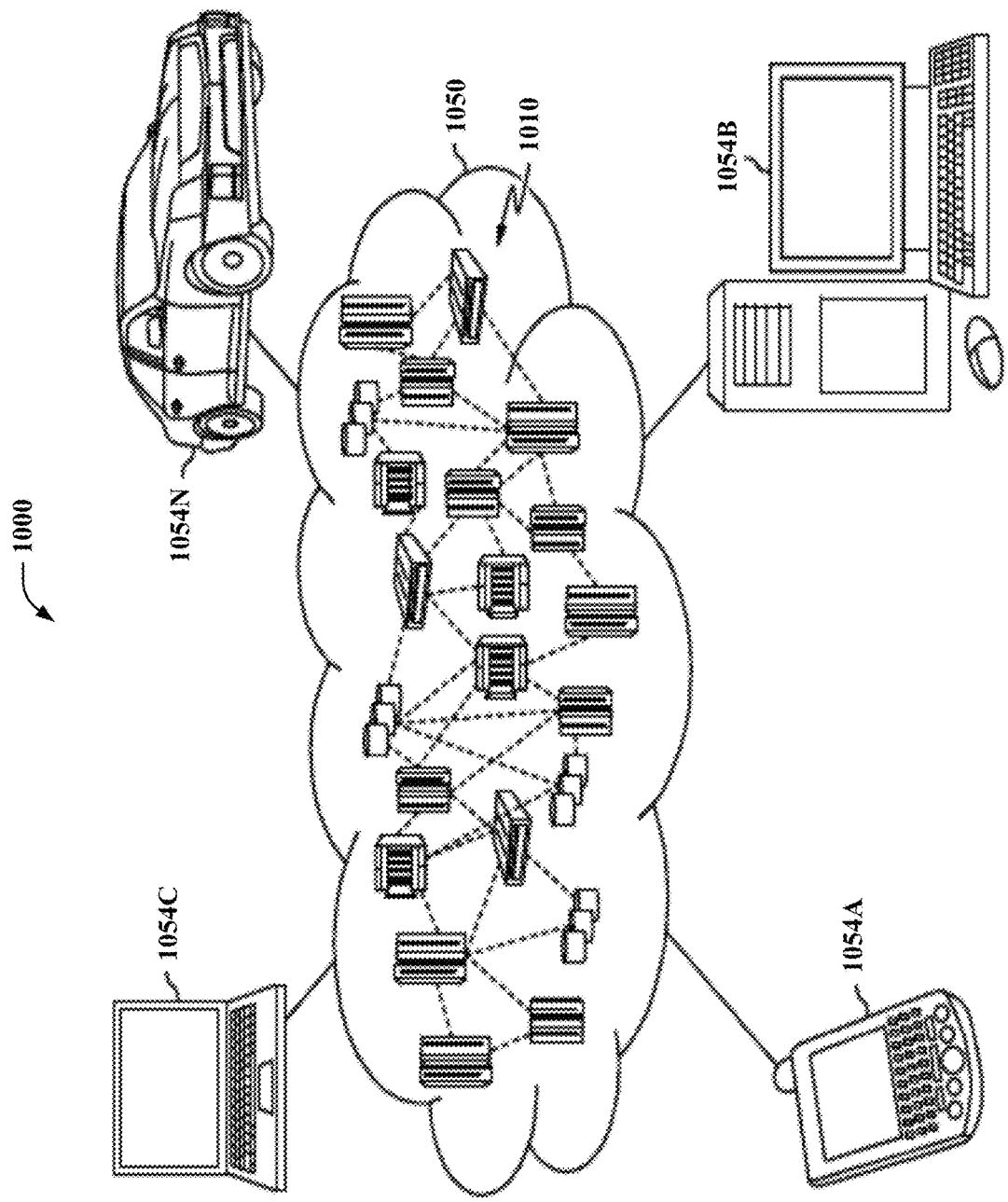
FIG. 10 depicts a cloud computing environment in accordance with one or more embodiments described herein.

Referring now to FIG. 10, an illustrative cloud computing environment 1050 is depicted. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

As shown, cloud computing environment 1050 includes one or more cloud computing nodes 1010 with which local computing devices used by cloud consumers, such as, for example, personal digital assistant (PDA) or cellular telephone 1054A, desktop computer 1054B, laptop computer 1054C, and automobile computer system 1054N may communicate. Although not illustrated in FIG. 10, cloud computing nodes 1010 can further comprise a quantum platform (e.g., quantum computer, quantum hardware, quantum software, etc.) with which local computing devices used by cloud consumers can communicate. Nodes 1010 may communicate with one another. They may be grouped (not shown) physically or virtually, in one or more networks, such as Private, Community, Public, or Hybrid clouds as described hereinabove, or a combination thereof. This allows cloud computing environment 1050 to offer infrastructure, platforms and software as services for which a cloud consumer does not need to maintain resources on a local computing device. It is understood that the types of computing devices 1054A-N shown in FIG. 10 are intended to be illustrative only and that computing nodes 1010 and cloud computing environment 1050 can communicate with any type of computerized device over any type of network and network addressable connection (e.g., using a web browser).

Figure 11:
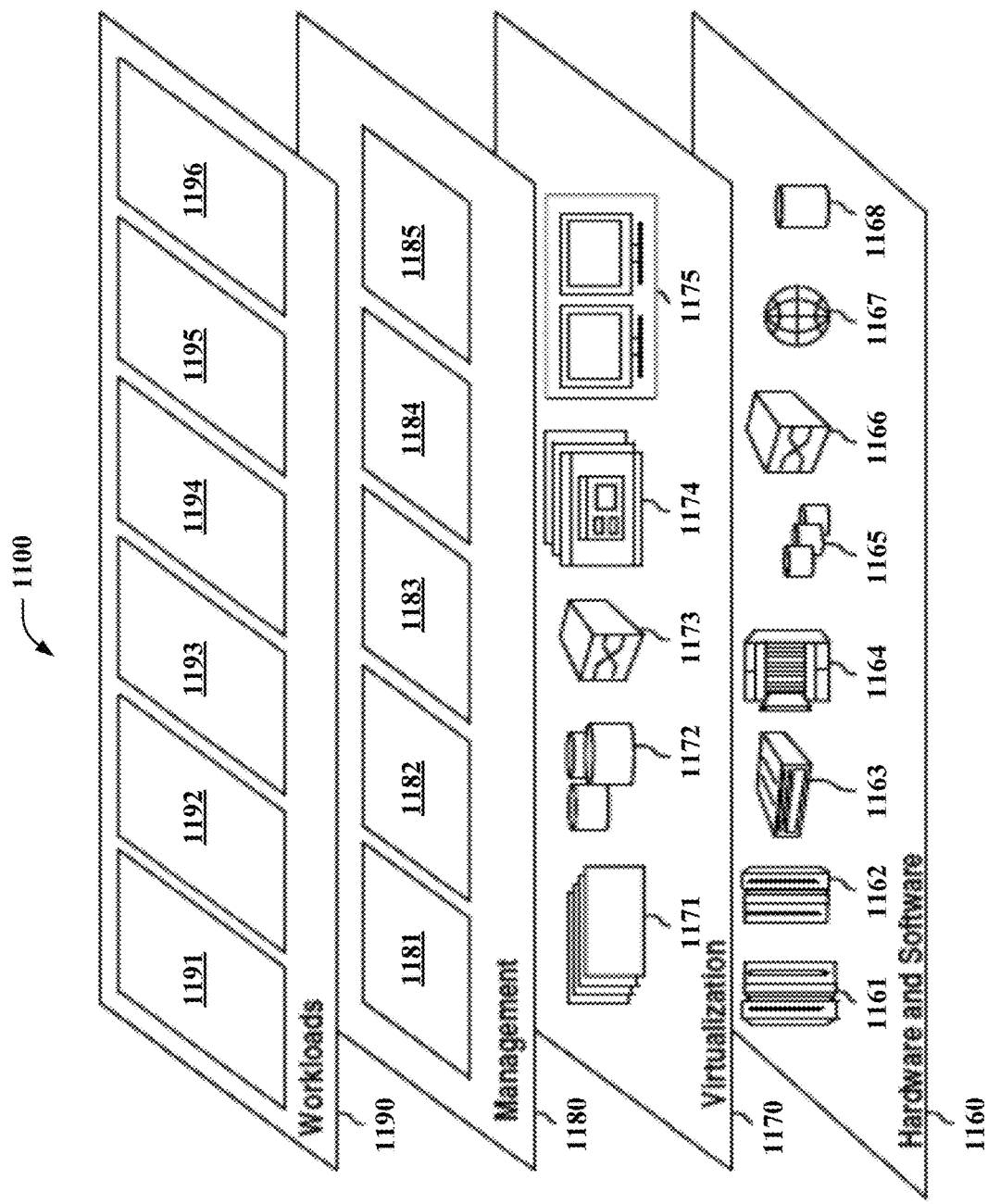
FIG. 11 depicts abstraction model layers in accordance with one or more embodiments described herein.

Referring now to FIG. 11, a set of functional abstraction layers provided by cloud computing environment 1150 (FIG. 11) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 1160 includes hardware and software components. Examples of hardware components include: mainframes 1161; RISC (Reduced Instruction Set Computer) architecture-based servers 1162; servers 1163; blade servers 1164; storage devices 1165; and networks and networking components 1166. In some embodiments, software components include network application server software 1167, database software 1168, quantum platform routing software (not illustrated in FIG. 11), and quantum software (not illustrated in FIG. 11).

Virtualization layer 1170 provides an abstraction layer from which the following examples of virtual entities may be provided: virtual servers 1171; virtual storage 1172; virtual networks 1173, including virtual private networks; virtual applications and operating systems 1174; and virtual clients 1175.

In one example, management layer 1180 may provide the functions described below. Resource provisioning 1181 provides dynamic procurement of computing resources and other resources that are utilized to perform tasks within the cloud computing environment. Metering and Pricing 1182 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1183 provides access to the cloud computing environment for consumers and system administrators. Service level management 1184 provides cloud computing resource allocation and management such that required service levels are met. Service Level Agreement (SLA) planning and fulfillment 1185 provide pre-arrangement for, and procurement of, cloud computing resources for which a future requirement is anticipated in accordance with an SLA.

Workloads layer 1190 provides examples of functionality for which the cloud computing environment may be utilized. Non-limiting examples of workloads and functions which may be provided from this layer include: mapping and navigation 1191; software development and lifecycle management 1192; virtual classroom education delivery 1193; data analytics processing 1194; transaction processing 1195; and quantum state measurement logic software 1196.

The present invention may be a system, a computer-implemented method, an apparatus and a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and a wireless network. The network can comprise copper transmission cables, optical transmission fibers, wireless transmission, routers, firewalls, switches, gateway computers and edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and block diagrams of computer-implemented methods, apparatus (systems), and computer program products according to embodiments of the invention. It will be understood that each block of the flowchart illustrations and block diagrams, and combinations of blocks in the flowchart illustrations and block diagrams, can be implemented by computer readable program instructions. These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and block diagram block or blocks. These computer readable program instructions can also be stored in a computer readable storage medium that can direct a computer, a programmable data processing apparatus, and other devices to function in a particular manner, such that the computer readable storage medium having instructions stored therein comprises an article of manufacture including instructions which implement aspects of the function/act specified in the flowchart and block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and block diagram block or blocks.

The flowchart and block diagrams in the Figures illustrate the architecture, functionality, and operation of possible implementations of systems, computer-implemented methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and flowchart illustration, and combinations of blocks in the block diagrams and flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and computers, those skilled in the art will recognize that this disclosure also can or can be implemented in combination with other program modules. Generally, program modules include routines, programs, components, data structures, etc. that perform particular tasks and implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

As used in this application, the terms "component," "system," "platform," "interface," and the like, can refer to and can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and a computer. By way of illustration, both an application running on a server and the server can be a component. One or more components can reside within a process and thread of execution and a component can be localized on one computer and distributed between two or more computers. In another example, respective components can execute from various computer readable media having various data structures stored thereon. The components can communicate via local and remote processes such as in accordance with a signal having one or more data packets (e.g., data from one component interacting with another component in a local system, distributed system, and across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and "exemplary" are utilized to mean serving as an example, instance, or illustration. For the avoidance of doubt, the subject matter disclosed herein is not limited by such examples. In addition, any aspect or design described herein as an "example" and "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random-access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
   a memory that stores computer-executable components; and
   a processor that executes the computer-executable components stored in the memory, wherein the computer-executable components comprise:
   a parameter selecting component that selects a first stimulus parameter based on a target area of an entity; and
   a mapping component that:
   generates, during a testing mode, for a defined region of a body of the entity, a first function corresponding to an stimulus map by mapping the first stimulus parameter to a response from the entity to application of a first neuromodulating stimulus; and
   generates, during the testing mode, for the defined region of the body of the entity, a second function, which is an inverse of the first function such that the response from the entity as an entity response parameter input to the second function results in a second stimulus parameter utilized as a stimulus input,
   wherein the stimulus map is incrementally generated over time based on a selection of parameters by the parameter selecting component, application of a stimulus, via the stimulus device, and based on the parameters, collection of response data via a response input device, and mapping of the stimulus to the result via the mapping component, and wherein, once the testing mode has ended and the therapeutic mode has begun, the mapping component: applies to the entity based on the first stimulus parameter, the first neuromodulating stimulus, to therapeutically cause or prevent a sensation, wherein the first neuromodulating stimulus is delivered via at least a first electrode or a second electrode of a stimulation device.

2. The system of claim 1, wherein the response comprises a result of an alteration of nerve activity of the entity by application of the first neuromodulating stimulus.

3. The system of claim 2, wherein the response further comprises a period of time from the application of the first neuromodulating stimulus until a steady state of nerve activity is achieved by the entity, wherein the steady state is a condition achieved when, for the entity, perception of sensation resultant from the nerve activity has no measurable change over time.

4. The system of claim 3, wherein the response further comprises a change in the nerve activity perceived by the entity during the period of time.

5. The system of claim 2, wherein the computer-executable components further comprise a therapeutic component that therapeutically alters nerve activity of the entity to achieve a nerve activity result from the entity based on the stimulus map.

6. The system of claim 2, wherein the computer-executable components further comprise:

a target area component that selects a target area of the entity, wherein the result comprises a response area of the entity where the alteration of nerve activity is perceived by the entity; and a sensation evaluation component that:

evaluates a similarity of the target area and the response area, and wherein the mapping component further maps the first stimulus parameter based on the similarity of the target area, the response area, and the target area; and augments, based on the evaluated similarity, the mapping performed by the mapping component.

7. The system of claim 6, wherein the augmentation comprises storing stimulus parameters identifying the response area at which the sensation of the nerve activity was perceived along with identifying a second response area at which the sensation of the nerve activity was also perceived, wherein the response area and the second response area are unintended response areas distinct from the target area.

8. The system of claim 6, wherein the augmentation comprises storing stimulus parameters substituting the response area at which the sensation of the nerve activity was perceived for the target area at which the sensation of the nerve activity was intended.

9. The system of claim 1, wherein the first stimulus parameter comprises a pulse-rate and a pulse width of a stimulation pulse.

10. The system of claim 7, wherein the mapping component further generates the stimulus map by mapping a second stimulus parameter to the response from the entity to application of the first neuromodulating stimulus and a second neuromodulating stimulus, wherein the second neuromodulating stimulus was applied to the entity based on the second stimulus parameter, and wherein the characteristic of the stimulation pulse comprises an interference compensating characteristic of the stimulation pulse.

11. The system of claim 1, wherein the stimulation device comprises a spinal cord stimulation device and wherein the first stimulus parameter comprises, for the first electrode and the second electrode, an electrode setting.

12. The system of claim 1, wherein the response from the entity is received by the mapping component based on input provided from the entity based on a graphical depiction of the entity.

13. The system of claim 1, wherein the mapping component generates the stimulus map based on a dermatome of the entity.

14. A computer-implemented method comprising:

selecting, by a device operatively coupled to a processor, a first stimulus parameter based on a target area of an entity;

generating, by the device, during a testing mode, for a defined region of a body of the entity, a first function corresponding to a stimulus map by mapping the first stimulus parameter to a response from the entity to application of a neuromodulating stimulus; and generating, by the device, during the testing mode, for the defined region of the body of the entity, a second function, which is an inverse of the first function such that the response from the entity as an entity response parameter input to the second function, wherein the stimulus map is incrementally generated over time based on a selection of parameters, application of the neuromodulating stimulus based on the parameters, collection of response data, and mapping of the neuromodulating stimulus to a result of application of the neuromodulating stimulus, and wherein, once the testing mode has ended and the therapeutic mode has begun, the method further comprises:

applying, by the device, to the entity based on the first stimulus parameter, the neuromodulating stimulus, to therapeutically cause or prevent a sensation, wherein the neuromodulating stimulus is delivered via at least a first electrode or a second electrode of a stimulation device.

15. The computer-implemented method of claim 14, further comprising displaying a visual mapping of a result of the applying the neuromodulating stimulus, wherein the visual mapping is displayed on a paresthesia map of the entity, and further comprising generating the stimulus map based on an analysis, by the device, of the paresthesia map.

16. The computer-implemented method of claim 14, wherein the stimulus parameter is selected, by the device, from the stimulus map based on a second result of a previous neuromodulating stimulus applied to the entity stored in the stimulus map.

17. A computer program product that maps a stimulus parameter to a sensation perceived by an entity, the computer program product comprising a non-transitory computer readable storage medium having program instructions embodied therewith, the program instructions executable by a processor to cause the processor to:

select, by the processor, a first stimulus parameter based on a target area of an entity;

generate, by the processor, during a testing mode, for a defined region of a body of the entity, a first function corresponding to a stimulus map by mapping the first stimulus parameter to a response from the entity to application of a neuromodulating stimulus; and generate, by the processor, during the testing mode, for the defined region of the body of the entity, a second function, which is an inverse of the first function such that the response from the entity as an entity response parameter input to the second function, wherein the stimulus map is incrementally generated over time based on a selection of parameters, application of the neuromodulating stimulus based on the parameters, collection of response data, and mapping of the neuromodulating stimulus to a result of application of the neuromodulating stimulus and wherein, once the testing mode has ended and the therapeutic mode has begun, the program instructions are further executable by the processor to cause the processor to:

apply, by the processor, to the entity based on the first stimulus parameter, the neuromodulating stimulus, to therapeutically cause or prevent a sensation, wherein the neuromodulating stimulus is delivered via at least a first electrode or a second electrode of a stimulation device.

18. The computer program product of claim 17, wherein the neuromodulating stimulus comprises a stimulation pulse delivered via a spinal cord stimulation device.

19. The system of claim 1, wherein, during the testing phase, the mapping component generates function-inverse function pairs for a plurality of regions of the body of the entity until defined criteria is met, and wherein the system begins therapeutic use once the defined criteria is met.

20. The system of claim 19, wherein the defined criteria comprises at least one of a defined level of accuracy or a defined level of coverage of different sensory areas of the entity.

* * * * *